United States Patent [19]

Laipply

[11] Patent Number: 4,696,393

[45] Date of Patent: * Sep. 29, 1987

[54] APPLICATOR WIPE FOR INVISCID FLUIDS

[76] Inventor: Thomas C. Laipply, 13530 Fox Den East, Russell, Ohio 44072

[*] Notice: The portion of the term of this patent subsequent to Jan. 24, 2001 has been disclaimed.

[21] Appl. No.: 781,236

[22] PCT Filed: Jan. 23, 1984

[86] PCT No.: PCT/US85/00120

§ 371 Date: Sep. 23, 1985

§ 102(e) Date: Sep. 23, 1985

[87] PCT Pub. No.: WO85/03275

PCT Pub. Date: Aug. 1, 1985

Related U.S. Application Data

[63] Continuation-in-part of Ser. No. 312,879, Oct. 19, 1981, Pat. No. 4,427,115, and a continuation-in-part of Ser. No. 312,880, Oct. 19, 1981, Pat. No. 4,427,111.

[51] Int. Cl.$^4$ .................. B65D 83/00; B65D 75/00
[52] U.S. Cl. ................................ 206/210; 206/441; 206/484; 206/812
[58] Field of Search ............... 206/484, 438, 441, 530, 206/229, 210, 812; 15/104.93

[56] References Cited

U.S. PATENT DOCUMENTS

| | | |
|---|---|---|
| 1,527,659 | 2/1925 | Wilkie . |
| 1,810,453 | 6/1931 | Webster et al. . |
| 2,621,784 | 12/1952 | Van Boythem . |
| 2,760,630 | 8/1956 | Lakso . |
| 3,025,957 | 3/1962 | Wall .................................... 206/440 |
| 3,035,300 | 5/1962 | Wattles . |
| 3,057,128 | 10/1962 | Gerhauser . |
| 3,057,467 | 10/1962 | Williams . |
| 3,240,326 | 3/1966 | Miller . |
| 3,280,420 | 10/1966 | Wanzenberg ........................ 53/410 |
| 3,439,469 | 4/1969 | Van Mil, Jr. . |
| 3,481,099 | 12/1969 | Clancy . |
| 3,485,349 | 12/1969 | Chaney . |
| 3,507,087 | 4/1970 | Pratt . |
| 3,527,400 | 9/1970 | Shepherd et al. . |

(List continued on next page.)

FOREIGN PATENT DOCUMENTS

644007 2/1964 Belgium .
613023 1/1961 Canada .

Primary Examiner—George E. Lowrance
Assistant Examiner—Brenda J. Ehrhardt
Attorney, Agent, or Firm—Renner, Otto, Boisselle & Lyon

[57] ABSTRACT

An integral alcohol preparation device (10) or like type of fluid applying device includes an absorbent material or pad (11) for containing alcohol or other fluid, a fluid impermeable material, for example of metal foil (20) lined with plastic (21), as a selectively openable fluid tight chamber for the pad and fluid contained therein, and the pad and fluid impermeable material being attached as a substantially integral assembly. Being so attached, a method of using such a fluid applying device, then, may include the steps of manipulating the fluid impermeable material to open the chamber and to expose the pad and fluid contained therein without breaching the integrity of the several parts individually or collectively, and applying the fluid from the pad to an external surface. Further, a method is disclosed for making an integral fluid applying device. In an alternate embodiment a one piece fluid applying device is formed of flexible material that is folded to form a chamber to contain a fluid. The flexible material is impermeable and unaffected by the fluid. A seal is formed about the chamber to maintain the fluid tight integrity thereof. Surface portions of the flexible material which form walls of the chamber also form surfaces for applying the fluid to another surface. For example, to the skin of a patient. Similar methods of use and manufacturing may be employed with both embodiments. In both embodiments the flexible fluid impermeable material may be a single piece or may be comprised of plural pieces fastened together, e.g., along an edge of the device, and intended to remain so fastened during use.

15 Claims, 38 Drawing Figures

U.S. PATENT DOCUMENTS
(See top sheet)

| | | |
|---|---|---|
| 3,542,634 | 11/1970 | Such et al. . |
| 3,580,254 | 5/1971 | Stuart . |
| 3,635,567 | 1/1972 | Richardson, Jr. . |
| 3,720,037 | 3/1973 | Jones . |
| 3,809,483 | 5/1974 | Young . |
| 3,862,684 | 1/1975 | Schmitt . |
| 3,903,345 | 9/1975 | Baker et al. . |
| 3,978,636 | 9/1976 | Clancy . |
| 3,986,640 | 10/1976 | Redmond . |
| 4,053,053 | 10/1977 | Tumanangday . |
| 4,265,234 | 5/1981 | Schaar ............ 206/441 |
| 4,304,333 | 12/1981 | Kozlow, Sr. ........ 206/484 |
| 4,342,395 | 8/1982 | Brown . |
| 4,372,098 | 2/1983 | Mason . |
| 4,427,111 | 1/1984 | Laipply . |
| 4,427,115 | 1/1984 | Laipply . |
| 4,555,022 | 11/1985 | Eagon et al. ....... 206/441 |

APPLICATOR WIPE FOR INVISCID FLUIDS

This application is a continuation-in-part of my copending U.S. patent applications Ser. Nos. 312,879 and 312,880, both filed Oct. 19, 1981 now U.S. Pat. Nos. 4,427,115 and 4,427,111 respectively. The entire disclosures of such applications are hereby incorporated by reference.

TECHNICAL FIELD

The present invention relates generally, as indicated, to fluid applying devices and methods and methods of manufacturing such devices.

The invention will be described in detail below as relating to an alcohol wipe device, which is a device that contains alcohol or like fluid intended for sterilizing, cleaning or like purposes. However, it will be understood that the invention encompasses use of fluids other than alcohol or containing alcohol and other materials for sterilizing, cleaning or other purposes; these may include, for example, iodine, perfume, bug repellant, stain remover, insect sting antiseptic, etc.

BACKGROUND OF PRIOR ART

Alcohol preparation devices or alcohol wipes have been known and used in the medical profession for a number of years. Such devices include alcohol absorbing material, such as a gauze or gauze-like material which contains alcohol, and a fluid-tight protective package that is sealed to define therein a chamber in which the absorbent alcohol containing material is contained. An example of one type of abosrbent material is disclosed in U.S. Pat. No. 3,542,634; such material is used in the Webcol alcohol prep device sold by the Kendall Company, Boston, Mass., for example, for the purpose of applying sterilizing isopropal alcohol to the skin of a patient. Another example of such absorbent material and a package for containing the same is disclosed in U.S. Pat. No. 3,057,467; the absorbent material is a folded towelette containing a particular fluid for cleansing and refreshing a user and the package material is, for example, and aluminum foil with a thermoplastic liner. Such package material is impervious to the fluid contained therein, including both the liquid and vapor or gas forms thereof. Such material also is impervious to air and other materials that might otherwise contaminate the fluid and absorbent material contained in the package. The '467 patent discloses polyethylene, polyvinyl resin or cellulose acetate as suitable thermoplastic materials for providing a protective coating on the foil and for providing the impervious vapor-proof barrier desired; such materials also are readily heat sealable to seal closed the package. Other materials of which the package disclosed in the '467 patent may be made are celluloic materials lined with a thermoplastic film or various synthetic or plastic materials. The device in the '467 patent is manufactured by forming a three part sandwich of two sheets of package material and the folded fluid impregnated towelette therebetween, and the edges of the package material sheets are heat sealed to each other about the entire perimeter of the package.

Several disadvantages inure to the prior fluid applying devices, such as the prior alcohol prep devices, towelette devices, etc. One disadvantage is that the package material must be torn to open the same in order to remove the absorbent material. Upon tearing of the package, the absorbent material may be torn, which may reduce usefulness thereof. Also, when the package is torn it may result in one and possibly two pieces and must be discarded, depending upon whether the tear fully severs one part from the other; and eventually the absorbent material also must be discarded separately. The separate discarding steps may waste time and may result in one or more pieces not reaching a proper waste container, e.g. a piece may drop on the floor and create a safety hazard. A further disadvantage particularly with respect to prior alcohol prep devices is that the user, such as a medical technician, nurse or physician, must physically touch surfaces of the absorbent material; this increases the potential hazard of contamination of the sterile condition of the absorbent material and frequent touching of that material oftens tends substantially to dry the skin of such user. Moreover, frequent flexing of the heat sealed package may result in loss of the seal integrity.

BRIEF SUMMARY OF THE INVENTION

With the foregoing in mind, the invention has as an objective overcoming of one or more of the above disadvantages of fluid applying devices, and especially those of the type known as alcohol preparation devices.

According to one aspect of the invention, a combined fluid storage and application device includes a sheet-like fluid impermeable material having generally symmetrical halves positioned in generally flat parallel overlying relation to each other, a pair of respective edges of said material halves being securely joined along an effective fold line as an effectively single integral sheet of said material halves, a temporary seal sealing said halves to each other along a temporary seal line which begins and ends at the fold line, a fluid retaining cavity having substantially flat parallel opposed wall surfaces formed by said halves, said fold line and said temporary seal line cooperating to define the periphery of said fluid retaining cavity, a fluid retaining pad disposed in said cavity and adhered to said sheet, and a separation mechanism for simultaneously applying separating force substantially symmetrically to both said halves of said sheet and to said temporary seal line without tearing said sheet, said separation mechanism including at least a portion thereof for applying simultaneously continuous separating force in multiple directions to open said sheet from folded condition fully exposing said cavity and said pad while the integrity of said sheet is maintained.

According to another aspect, the invention includes a combined fluid storage container and applicator device for relatively inviscid fluids such as alcohols and iodine, said device including a sheet-like fluid impermeable material having generally symmetrical halves positioned in generally flat parallel overlying relation to each other, a pair of respective edges of said material halves being securely joined along an effective fold line as an effectively single integral sheet of said material halves, a temporary seal means sealing said halves to each other along a temporary seal line beginning and ending at said fold line forming a cavity enclosing fluid between said halves and within said temporary seal line and said fold line, a generally non-gaseous fluid or fluid-like material in said cavity, and a separation mechanism for simultaneously applying separating force substantially symmetrically to both said halves of said sheet and to said temporary seal without tearing said sheet, said separation mechanism including at least a portion thereof for applying simultaneously continuous separating force to open said temporary seal along the entire length of said seal line to form a flat surface covered with the fluid while the integrity of said sheet is maintained.

According to yet another aspect, a method of using a fluid applying device in which containment means for containing fluid material is attached to a fluid impermeable means that is sealed to form a fluid tight chamber for such fluid contained by the containment means comprises manipulating the fluid impermeable means to open the chamber and to expose the containment means without separating the device into multiple parts and applying such fluid from the containment means.

According to yet another additional aspect, a method of making a fluid applying device comprises attaching a fluid containment means and a fluid impermeable material and sealing the fluid impermeable material to retain the fluid containment means therein.

Another aspect of such methods of making a fluid application or wiping device, whether it be of integral type (one-piece) or not, relates to securement of the pad to the material. Such method includes adhering an absorbent pad to the essentially flat surface of a layer of an impermeable and adherable material by affixing a sufficient central area of pad and/or sufficient peripheral areas, e.g. edges or corners, of the pad to secure and stabilize the pad in a defined location on the impermeable material preventing any significant movement of the pad relative to the impermeable material during opening or use of the fluid storage and application devices, with such process not involving formation of any recessed or otherwise molded areas in the impermeable material to help align and fix the pad and produce a more even (flush) surface for covering by a separate second layer or folded over layer of impermeable material. Preferably such method is carried out in an automated or continuous in-line process using essentially available equipment for manufacturing a fluid application device. Such method allows for use of thinner and cheaper component materials and faster automated equipment compared with the prior art pad fastening devices, which require a relatively thicker grade of foil material and therefore are more expensive and slower than the present invention.

According to an additional aspect, a method of applying a liquid to an external surface includes opening the seal of a chamber formed by flexible material having interior, non-porous, fluid impermeable wall surfaces that ordinarily exclusively bound the chamber and on which liquid from the chamber is coated, and wiping such surfaces to apply the liquid to such external surface.

An important aspect of the invention is that the device is so constructed that during use of the alcohol wipe, etc. there is no ordinarily intended separating of the device into a use portion and a throw-away portion. Rather the fluid impermeable material, and a fluid absorbing pad, if used, attached thereto, is intended to remain as a single integral structure both during storage, during opening, i.e. preparation for use, and during actual use; after such use the still singular structure device may be discarded. It will be appreciated that this integrity can be accomplished whether the fluid impermeable material actually is a single sheet, for example, or a plurality of sheets that are bonded, fastened, secured or otherwise held together to act as a single sheet when the device is closed or is opened for use. Therefore, as used herein single sheet and integral sheet of such fluid impermeable material means such a sheet comprised of one piece only or of plural pieces secured to remain ordinarily as one piece.

To the accomplishment of the foregoing and related ends, the invention, then, comprises the features hereinafter fully described in the specification and particularly pointed out in the claims, the following description and the annexed drawings setting forth in detail certain illustrative embodiments of the invention, these being indicative, however, of but several of the various ways in which the principles of the invention may be employed.

BRIEF DESCRIPTION OF THE DRAWINGS

In the annexed drawings.

BRIEF DESCRIPTION OF PRIOR ART FLUID APPLYING DEVICES

Figures 1A, 2A:
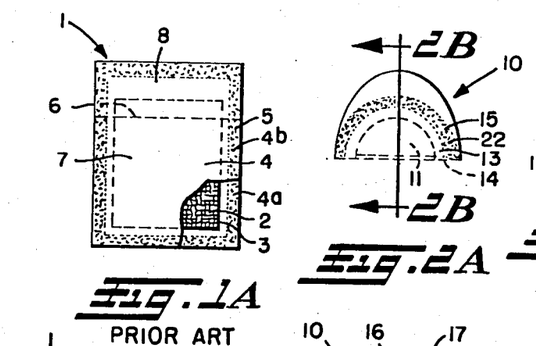
FIGS. 1A and 1B are plan views of a prior art fluid applying device of the alcohol preparation type or alcohol wipe type.
FIG. 2A is a plan view of an integral alcohol preparation device in accordance with the present invention in sealed or closed condition.
Figures 1B, 2C, 2D, 3, 4, 5, 6A, 6B:
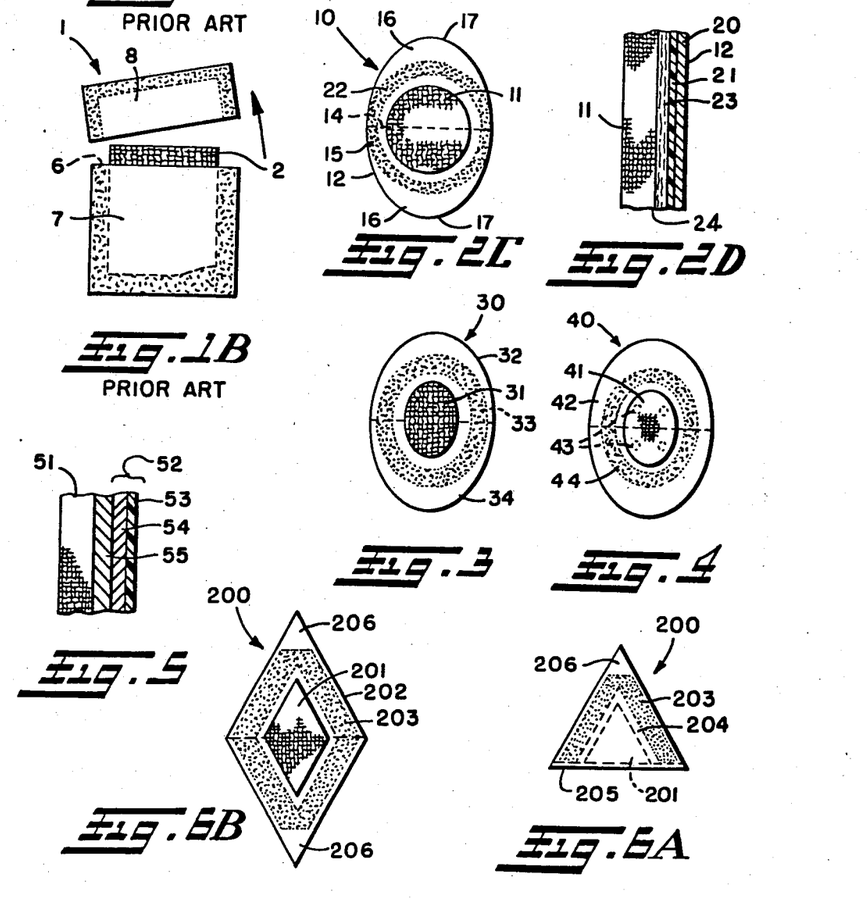
FIG. 2C is a plan view of the alcohol preparation device of Fig. 2A open and ready for use.
FIG. 2D is an enlarged fragmentary section view of a portion of the device of FIG. 2C.
FIG. 3 is a plan view of an alternate integral fluid applying device shown open and ready for use.
FIG. 4 is a plan view of another alternate fluid applying device open and ready for use, such device employing an alternate form of attachment means.
FIG. 5 is an enlarged fragmentary view of an integral fluid applying device using another form of attachment means.
FIG. 6A and 6B are plan views in the sealed and open conditions of a triangular/diamond integral fluid applying device.
Figure 2B:
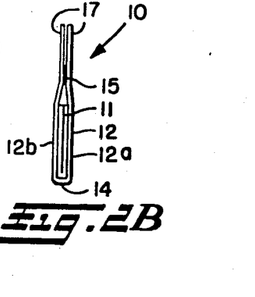
FIG. 2B is a section view of the alcohol preparation device looking generally in the direction of the arrows 2B—2B of FIG. 2A.

Referring briefly to FIGS. 1A and 1B, a prior art alcohol preparation device or alcohol wipe of the type mentioned above with reference to the Webcol device and the '634 and 467 patents is shown at 1. The device 1 includes a pad 2 of absorbent material for containing alcohol, such as, for example, a 70% isopropyl alcohol liquid. The pad 2 is contained in a chamber 3 formed in a package 4. The package 4 typically is formed of a metal foil that is coated or lined with thermoplastic material, for example, as is disclosed in the '467 patent. The lining material faces the chamber 3 so as to provide a fluid impermeable barrier to prevent escape of the alcohol by leakage, evaporation, or the like. The metal foil also provides a fluid impermeable barrier not only for the alcohol but also to prevent contamination of the materials in the chamber 3 from outside the package 4. The foil also provides additional support strength for the device 1. The package 4 is formed of two sheets 4a, 4b of such lined foil material, and the sheets are heat and/or pressure sealed to each other at respectively adjacent overlapping edges thereof around the perimeter of the device 1. The seal is indicated at 5 FIGS. 1A and 1B.

A dashed line 6 in FIG. 1A is the tear line separating the main body 7 of the package 4 and a tear strip portion 8 thereof. During use of the device 1 a user tears the same approximately along the tear line 6 to separate the tear strip 8 in the manner shown in FIG. 1B exposing the chamber 3 and the pad 2 therein. Usually the tear strip 8 is totally separated from the body 7 and is discarded. After the pad 2 has been removed from the body 7, the latter also is discarded and the pad may be grasped manually by a user to apply alcohol to the surface, for example, the skin of a patient. The pad 2 subsequently may be discarded.

DETAILED DESCRIPTION OF THE INVENTION

As distinguished from the intentionally separable parts of the prior art device 1, the integral fluid applying device in accordance with the present invention does not have intentionally separable parts and can in fact be stored and used without destroying the attached or structural integrity of the several parts.

Referring now in detail to the drawings, wherein like reference numerals designate like parts in the several figures, and initially to FIGS. 2A through 2D, an integral fluid applying device in accordance with the preferred embodiment and best mode of the present invention is shown at 10. The device 10 includes a pad 11 attached to the fluid impermeable material 12, which may be closed in the manner shown in FIGS. 2A and 2B to form a fluid-tight chamber that may be opened in the manner shown in FIG. 2C to expose the pad 11 for use to apply fluid contained therein. The pad 11 is circular shape and the package 12 is oval shape, as is seen in FIG. 2C. Such shapes cooperate so that when the device 10 is folded (FIGS. 2A and 2B) along the fold line 14, the seal 15 may be a semi-circular annulus providing a minimum size for the chamber 13, on the one hand, while permitting the outlying portions 16 of the material 12 to form generally overlapping, but unsealed, tabs or flanges 17 which may be used to open the device 10 from its closed condition breaching the integrity of the seal 15.

The pad 11 may be formed of natural or synthetic material or a combination thereof. An example of the material of which the pad may be formed is conventional gauze material, material disclosed in the '634 patent, material of the type used in the Webcol device, foldable material of the type disclosed in the '467 patent, and the like. It is intended that the pad 11 be a fluid containment means, and, therefore, such pad preferably is of a type of material that is absorbent of and permeable to the particular fluid it is intended to contain. Preferably such fluid is one containing alcohol, such as a 70% isopropyl alcohol mixture with water. Another fluid may be iodine, betadyne preparations, and other antiseptic solutions. Another example of a fluid that may be contained in the pad 11 is that disclosed in the '467 patent as a cleansing and refreshing agent. Other types of fluids, e.g. as mentioned above, and preferably inviscid fluids, also may be contained in the pad 11, such fluids most preferably ordinarily taking a liquid form with the sealing of the chamber 13 preventing the loss by leakage or evaporation until the device 10 is intended for use.

The fluid may be applied to the pad 11 by soaking or by an injection technique. The dimensions of the pad 11 preferably are smaller than those of the material of which the package 12 is formed to facilitate sealing of the package to form the chamber 13 and, additionally, to facilitate opening the package, for example by use of the flanges 17. The pad may be of fixed size or may be capable of unfolding (FIG. 16), and it may be on one side of the material of which the package 12 is formed, e.g. see FIGS. 9, 10, 15, 18A and 19, or it may be on both sides of the package, e.g. see FIGS. 2C, 3, 4, 7B, 8A, 8B, 14, 16, 17A and 17B. The material of which the pad 11 is formed should not be affected by the fluid it is intended to contain. Moreover, the pad 11 may be of a selected texture; for example, a rougher, more porous fibrous material may facilitate adhesion to the package material 12 and may provide some measure of abrasion when applying fluid to the skin of a patient, whereas a less textured material may retain larger quantities of fluid.

The material of which the package 12 is formed preferably is a metal foil 20 (FIG. 2D), such as aluminum foil and a thermoplastic liner 21, such as a polyethylene material, a polyvinyl resin, or a cellulose acetate. Alternatively, the foil 20 may comprise a cellulosic material lined with a thermoplastic film or other synthetic or plastic materials. Such materials are of the type disclosed in the '467 patent. Another example of material 12 is a foil-lined paper, which is relatively inexpensive.

The package material 12 should be relatively strong to resist unwanted penetration and it should be impermeable to ordinary external contaminants, such as air, dust, bacteria, etc., and impermeable to the fluid contained in the pad 11. Moreover, the material 12 should be unaffected by such fluid. The material 12 should be relatively flexible to permit ordinary manipulation and flexing that may occur during packaging, storage, and preparation for use, and it should be capable of being folded, for example, along the fold line 14, while maintaining the mechanical integrity of the material so that the zone in which the fold occurs remains as a fluid tight boundary for the chamber 13. The material 12 also should be attachable to the pad 11 by various means and techniques that will be described in greater detail below in order to form an integral device that during ordinary use is not intended to encounter separation of the pad 11 from the material 12. Further, the material 12 should be capable of being sealed at the seal zone 22 by thermal, mechanical, or other means. The material 12 should have adequate strength so that the force applied to the flanges or tabs 17 may be transmitted to the seal zone 22 in order to provide a relatively facile selective controlled opening of the device 10 while breaching the integrity of the seal 15 without damaging the integrity of other portions of the device 10.

The material 12 should be a single or integral piece of material or should function as such. For example the material 12 may be a single sheet. Alternatively and equivalently, the material 12 may be formed by two sheets securely joined, for example, at or at what will become the fold line 14 or area thereof. Such a joining or juncture of multiple sheets may be effected before folding at the fold line or may be effected during manufacturing of the device, e.g. whereby two such sheets are placed with overlying perimeter edges and one edge is securely bonded while the other(s) are sealed to form the breakable seal 15.

When it is very undesirable to get fluid from pad 11 on the fingers of a user of the device 10, e.g. when the fluid stains as does iodine, the radial dimension of the seal zone or the radial spacing of the seal zone inward from the periphery of the device 10 should be relatively large so the user will not get fluid on his fingers during use of the opened device 10. Such perimeter zone may be grasped by such user during such use. Such recessing of the seal also is useful to help avoid contamination.

The device 10 is oval in shape (FIG. 2C) and half-oval in shape when folded (FIG. 2A). The cooperative relation between the shape of the material 12 and that of the pad 11 is such that preferably the pad has smaller dimensions than the package material 12 to assure that the pad will be fully contained within the sealed chamber 13.

Figures 7A, 7B, 8A, 8B, 8C, 9, 10, 11:
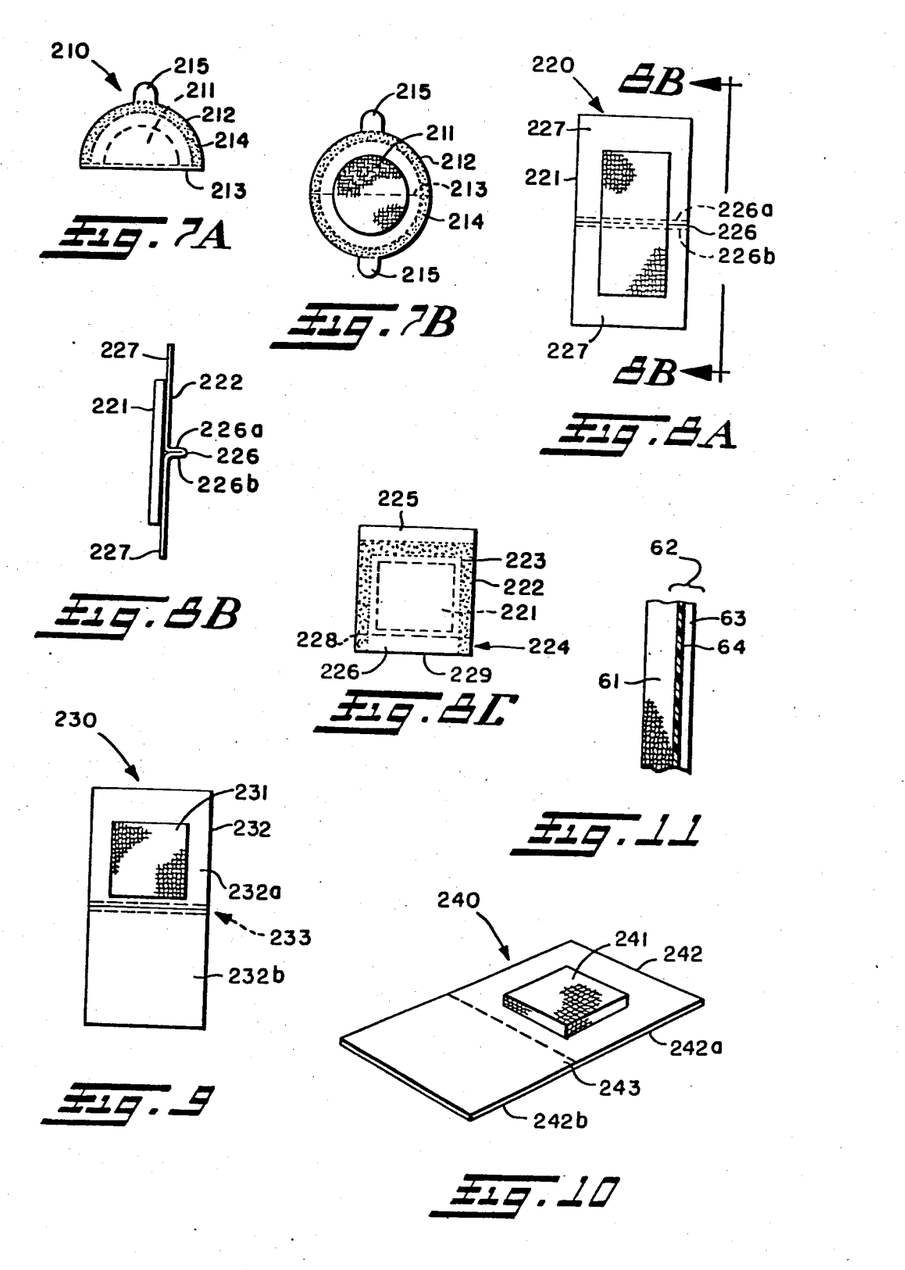
FIGS. 7A and 7B are plan views in the sealed and open conditions of a semi-circular/circular integral fluid applying device.
FIGS. 8A, 8B and 8C are open plan, side elevation and closed plan views of a rectangular integral fluid applying device with a user grasp tab or handle.
FIG. 9 is a plan view of an alternate integral fluid applying device in the open condition and in which the fluid containment material is on ony one-half of the fluid impermeable/package material.
FIG. 10 is an isometric view of an integral fluid applying device similar to that shown in FIG. 9 but in which one-half of the fluid impermeable/package material is intended to be folded back or torn off relative to the other portion to which the fluid containing material is attached.
FIG. 11 is an enlarged fragmentary section view of a direct connection mechanism for an integral fluid applying device in accordance with the invention.

The oval shape or other curved shape, such as the circular form of FIGS. 7A, 7B is very advantageous relative to a triangular/diamond shape (FIGS. 6A, 6B) or rectangular shape (FIGS. 8A–8C) because there are no sharp corners protruding that possibly could cause an injury or discomfort to a user, to avoid the possibility of a sharp corner getting caught in a crevice such that removal therefrom would cause the device to open, and to minimize tearing of the package 12. The oval configuration provides the relatively large flanges 17 while requiring a relatively minimum quantity of material 12. The curved form, as well as the triangle/diamond form (FIGS. 6A, 6B) facilitate opening of the integral fluid applying device without tearing of the same by controlled application and a distribution of forces in a gradual and spreading manner to the seal zone 22; such forces also are applied such that more of the force is of a tensile type both at the outset of breaching the seal integrity and as the two portions 12a, 12b, for example, of the package 12 continue to be separated. In contrast, in a rectangular shape device the sheer component of force applied to the seal zone would be greater, would require greater force overall to open the device, and, additionally, would be more likely to effect a tearing of the material 12 itself. If desired, one of the flanges 17 may be longer than the other in order to facilitate separating them and opening of the device 10. In any event, it is desirable that the device be so designed that a substantially balanced force can be applied simultaneously along two edges, edge areas, or even the same edge during opening of the seal 15.

Seal 15 is a heat seal or pressure seal or a combination thereof. Specifically, it may be formed by applying heat in the seal zone 22 in order to cause a bonding of the thermoplastic liner 21 on opposite portions 12a, 12b of the package material 12. Pressure may be applied to assure good bonding characteristics in order to maintain a highly integral seal achieving substantially complete isolation of the chamber 13 from the environment external of the device 10. The seal may be formed in a variety of conventional manners, such as that disclosed in the '467 patent. If desired, crimping, additional adhesive material, bonding material, or various liquid, semi-solid or solid materials may be applied at the seal zone 22 to respond to temperature, pressure, or other means for effecting a desired seal 15. Furthermore, the seal 15 preferably is capable of being broken to breach the integrity thereof when a force is applied to the tabs 17 in order to separate the portions 12a, 12b making the pad 11 accessible, to break generally uniformly during application of a balanced force thereto, and to avoid substantial tearing of the material 12.

Preferably the seal 15 is formed between opposed portions 12a, 12b about the periphery or perimeter of the device 10 where there is no fold 14. However, the fold 14 completes the sealed integrity of the chamber 13. On the other hand, if the portions 12a, 12b were totally separate pieces, the seal provided by the fold 14 would be provided by the material and/or means similar to those described above with respect to the remainder of the seal 14, for example, but would be so secure that the same would not break during ordinary use of the device 10. The material of which the seal is made should be unaffected by the fluid contained in the pad 11 and the seal should have adequate strength for relatively long term storage of the pad 11 without loss of the fluid from the chamber 13. The seal should be capable of being broken, as was noted earlier, with suitable force that will not damage the physical integrity for the remainder of the package material 12.

Very importantly the pad 11 is attached to the package material 12. As is illustrated in FIG. 2D, such attachment is effected by an interface material 23 between the pad surface 24 and the plastic liner 21. The interface material 23 preferably is a material known as PARAFILM sold by the American Can Company, Dixie/Marathon of Greenwich, Ct. Such interface material may be interposed between the pad 11 and plastic liner 21 and heat may be applied to one or both sides, for example, to the foil 20 and/or through the pad 11 causing the interface material 23 to tend to bond with the surface 24 and with the plastic liner 21. The shape of the interface 23 may be identical to the circular shape of the pad 11; alternatively the interface material may be larger or smaller in plan dimensions than the pad 11 or it may be in several pieces spaced at different places between the pad 11 and plastic liner 21, as may be desired to achieve the desired holding strength while minimizing the amount of interface material required for retention. The interface material 23 also should be unafffected by the fluid in the pad 11 and should be non-reactive chemically with any of the materials with which it comes in contact or proximity.

Other types of techniques may be used to attach the pad 11 to the package material 12. For example, glue (FIG. 4), tape (FIG. 5), a direct heat seal (FIG. 11), an interposed plastic or plastic-like material (FIG. 12), a solvent (FIG. 13), or a frame-like cover (FIGS. 18A, 18B and 19) may be used for the purpose of holding the pad to the package material.

The pad may be attached to the package material either prior or subsequent to application of fluid to the pad; however, preferably, the attachment is effected prior to delivery of the fluid to the pad. In particular, when a solvent or other curable adhesive, such as glue, is used to perform the attaching function, or when heat is necessary to effect attachment, it is desirable to permit solvents to evaporate or to permit the pad to cool before the fluid, such as alcohol, is applied to the pad. The interface material 23 also may be of a fluid impermeable type so as to cooperate further with the plastic liner 21 (or the liner 21 may be eliminated when a suitable interface material is used that will provide the fluid impermeability and suitable adherence to the foil or other material of which the outer layer of the package 12 is formed). Thus, the interface material 23 may enhance the integrity of the seal 15. Moreover, the interface material 23 may be used to provide such seal function; for example, PARAFILM may be sealed in response to application of thermal energy in the same way that the plastic liner 21 (if used) may be sealed to maintain the fluid tight integrity of the chamber 13. The strength of attachment of the pad 11 to the package material should be adequate so that the two materials do not separate during ordinary usage of the device 10. The attachment of the pad 11 to the package material 12, then, should have suitable sheer strength due to the usual rubbing action that the device 10 will undergo when applying fluid to a surface; whereas the tensile strength of the connection between the pad and package material is not quite as critical. The attaching material or technique also should be non-toxic for the device 10 often is used with humans, and, accordingly, the preferred PARAFILM quite clearly is non-toxic. Other than PARAFILM, other types of wax, saturated hydrocarbons, paraffin, or like materials also may be used for attaching the pad 11 to the package material 12. Such materials tend to provide an excellent bond, are unsticky when solidified, clearly are non-toxic, do not contain organic solvents, and would not hinder opening of the seal 15. Gelatin also may be used for attaching the pad to the package material; but gelatin ordinarily is more difficult to work with than the preferred wax material.

Summarizing, then, a device 10 in accordance with the present invention includes a means (the pad 11) for absorbing and containing fluid, a means (the package material 12) that provides an impermeable barrier to the fluid while also permitting mechanical flexibility of the device, attachment of the foregoing means to make the device integral, and an externally applied, e.g. by force, heat, or the like, seal 15.

A device 10 in accordance with the present invention may be manufactured, for example, by the following steps. The package material 12 is cut to the desired shape. For example, such package material may include foil already coated with a plastic liner. A fold or crimp may be applied (FIGS. 8A–8C) if a handle is to be provided on the device. The interface material 23 is placed into engagement with or applied to the package material, and then the pad 11 is applied by placing the same into engagement with the interface material. Heat is applied to cause the interface material to bond with the pad 11 and package material 12. (If the heat were to cause a disruption of the plastic liner 21, the interface material 23 may provide compensation therefor.) Alcohol or other fluid is applied to the pad 11, and the device then is folded, for example to the configuration shown in FIGS. 2A and 2B. The seal is formed by applying heat and/or force to the perimeter of the device defining the area of the chamber 13 while preferably not bonding the flanges 17 together, which should remain separable for facile manual grasping and opening of the device 10.

An alternative method includes the step of bonding or otherwise securing, e.g. by crimping, heat sealing, adhesive, etc., two sheets 12a, 12b (FIG. 2B) to form a single integral sheet 12. Such bonding, etc., may be carried out before folding or it may be carried out in lieu of folding, specifically whereby the two sheets of material 12a, 12b are placed in overlying position with the pad 11 sandwiched therebetween, and the bond and seal 15 then may be formed.

The methods or obviously modified versions thereof may be carried out to make the several embodiments of wiping devices disclosed herein.

Another aspect of such methods of making a fluid application or wiping device, whether it be of integral type (one-piece) or not, relates to securement of the pad 11 to the material 12. Such method includes adhering, e.g. heat sealing, an absorbent pad to the essentially flat surface of a layer of an impermeable and adherable, e.g. heat sealable, material 12 by affixing, e.g. heat sealing, a sufficient central area of the pad and/or sufficient peripheral areas, e.g. edges or corners, of the pad to secure and stabilize the pad in a defined location on the impermeable material preventing any significant movement of the pad relative to impermeable material during opening or use of the fluid storage and application devices, with such process not involving formation of any recessed or otherwise molded areas in impermeable material to help align and fix the pad and produce a more even (flush) surface for covering by a separate second layer or folded over layer of impermeable material. Preferably such method is carried out in an automated or continuous in-line process using essentially available equipment for manufacturing a fluid application device. Such method allows for use of thinner and cheaper component materials and faster automated equipment compared with the prior art pad fastening devices, which require a relatively thicker grade of foil material 12 and therefore are more expensive and slower than the present invention.

To use the device 10, the same may be held by a user and manipulated to open the device exposing pad 11. More specifically, the flanges 17 may be grasped between the thumb and forefinger, for example, of both hands of the user and force tending to separate the flanges may be applied. Such force should be adequate to break the seal 15 allowing the device 10 to be opened along the semi-circular seal zone in response to a balanced force application thereto. When the device is fully open, whereupon the fold 14 or bonded area is straightened so that the device is substantially flat in the manner shown in FIG. 2C, the user may grasp one of the flanges 17 between thumb and forefinger while using the fingers of the same hand against the package material 12 behind the area in which the pad 11 is located to provide a backing therefore; and the pad may be rubbed against a surface, such as the skin of a patient, to apply fluid from the pad to the surface, e.g. for sterilizing, cleansing or like purposes. Importantly no part of the device 10 is intended to be torn away from another and discarded before or during use.

Referring now to FIG. 3, a modified device 30 is shown there. The device 30 includes an oval shape pad 31 and oval shape package material 32, which are similar to the pad and package materials 11, 12 described above. The pad 31 and package material 32 may be secured to together by the various techniques disclosed herein. An advantage to the configurational device 30 is that the oval pad 31 may have a larger surface area exposure relative to the size of the package material 32 than does the circular pad 11 of FIG. 2C, for example. However, a disadvantage to the device 30 relative to the device 10 is that the seal zone 33 will take on a half-oval shape that reduces the effective free area of the respective tabs 34, thus reducing the exposed area thereof available to be grasped by a user to open the device 30. Although the device 30 is shown in its open position, it will be appreciated that such device may be folded over and sealed in the manner described above with reference to the device 10.

Turning now to FIG. 4, the integral fluid applying device 40 includes an oval pad 41 attached to oval package material 42 of the types described above with reference to the device 10. However, in the device 40 glue 43 or like adhesive is used to effect attachment of the pad 41 to the liner, for example, of the package material 42. The device 40 is shown in open condition, although the seal zone 44 is shown, and such zone ordinarily would provide a complete seal for the device 40 in the manner described above with reference to the seal 15.

Various types of solvent or solvent base materials may be used for the glue or adhesive 43. Preferably the fluid intended to be applied to the pad 41 is not applied thereto until such solvents would evaporate. A preferred adhesive, which has been found ordinarily to be non-toxic and highly effective, is Ross Rubber Cement sold by Ross Chemical Co., Detroit, Mich. The various glues 43 may be applied by dabbing, rollers, swabbing, spraying, and the like.

In FIG. 5 is a fragmentary view of a technique for attaching a pad 51 to a package material 52, which includes a foil material 53 and a thermoplastic liner 54. Such technique employs tape 55 which may be a type of tape having adhesive material on both the sides thereof.

Jumping to FIG. 11, another attachment technique for attaching a pad 61 to package material 62 of an integral fluid applying device is illustrated. Such package material 62 includes, for example, a foil material 63 and a thermoplastic liner 64. Such thermoplastic liner 64 preferably has suitable thickness and is adequately responsive to application of thermal energy thereto in order to maintain the fluid tight integrity of the chamber formed in the fluid applying device, such as the chamber 13 described above, while also in response to the applied thermal energy forming a bond with the pad 61. It is noted here that since the bond ordinarily should be relatively strong to shear forces, the small degree of melting of the plastic liner 64 and interfacing of the surface thereof with a relatively rough surface of the pad 61 will provide a good measure of shear force retention. On the other hand, although the penetration of the plastic material of the liner 64 ordinarily would not be very deep into the pad 61, the same is not essential since it usually will not be necessary for the bond therebetween to be resistive to high levels of tensile force.

Figures 12, 13, 14, 15, 16, 17A, 17B:
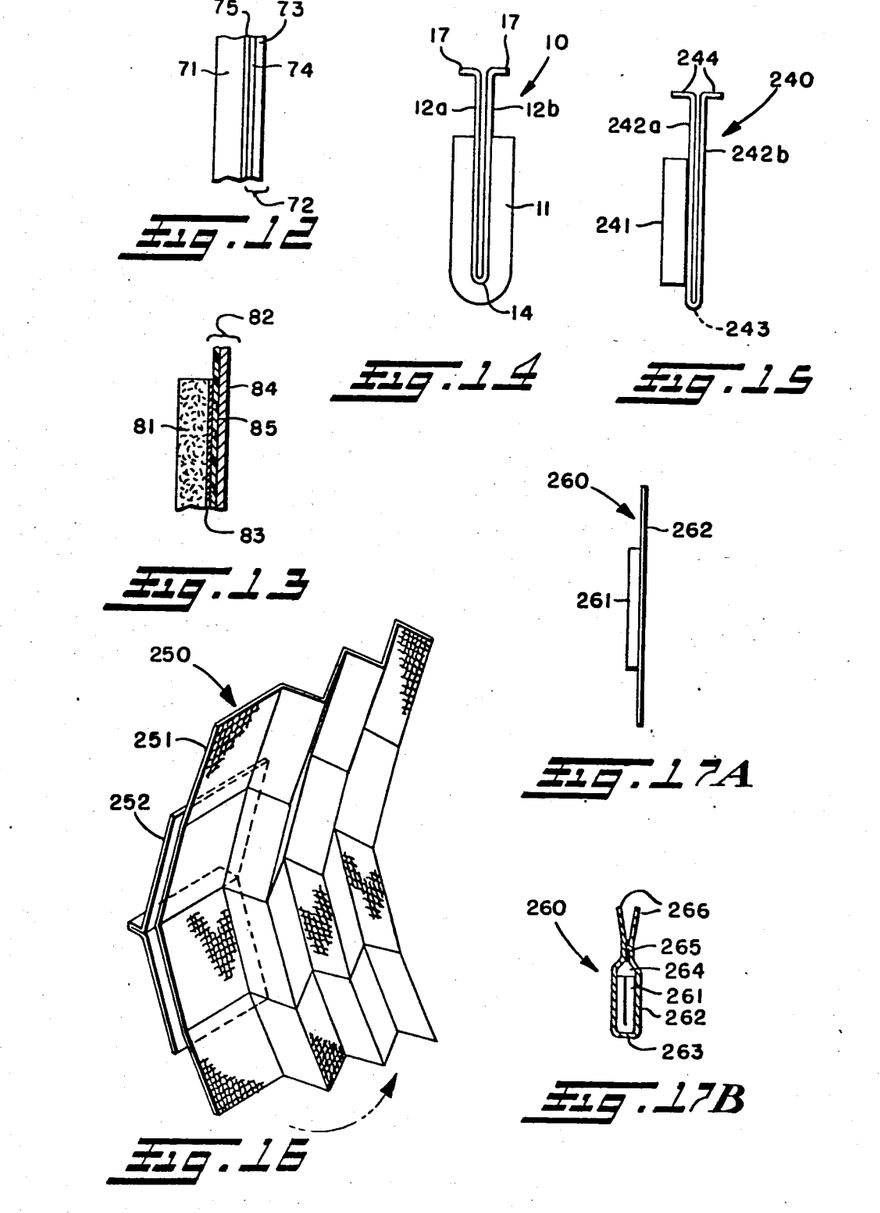
FIGS. 12 and 13 are enlarged fragmentary section views of additional attachment mechanisms for attaching the fluid containment material to the fluid impermeable/package material in accordance with the invention.
FIGS. 14 and 15 are schematic plan views of respective integral fluid applying devices showing a manner of use in which the two portions of fluid impermeable/package material are reverse folded.
FIG. 16 is an isometric view of a towelette type of integral fluid applying device.
FIGS. 17A and 17B are side elevation and section views, respectively, of a two part integral fluid applying device shown in open and closed conditions, respectively.

The fragmentary view of FIG. 12 is another example of a technique for attaching a pad 71 to package material 72, which includes a foil 73 and a thermoplastic material 74, for example. Such technique employs the use of a plastic interface material 75, such as plastic wrap, for example the type sold under the trademark Saran.

In FIG. 13 the pad 81 is attached to the package material 82 by a solvent represented at 83. The package material 82 again may be of a foil 84 having a plastic liner 85. The solvent 83 preferably affects both that portion of the pad 81 and that portion of the liner 85 with which it comes in contact so s to effect a bond between those respective portions. A synthetic sponge would be an example of a suitable solvent responsive material as the pad 81.

Various techniques described above for attaching a fluid absorbent pad, such as pad 11 to fluid impermeable material, such as the package material 12 of the device 10, may be employed in the various embodiments of the integral fluid applying devices of the invention disclosed herein and equivalents thereof.

Figure 18A:
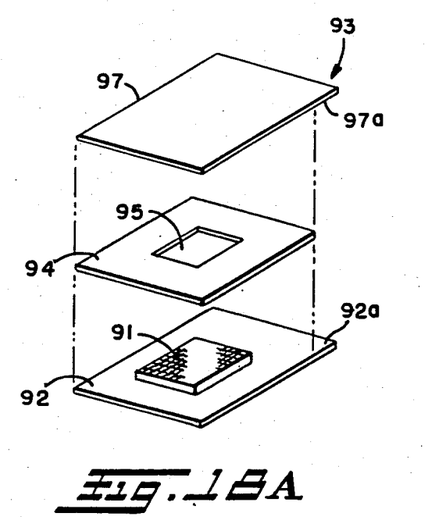
FIGS. 18A and 18B are, respectively, exploded isometric and side section views of a sandwich construction of integral fluid applying device employing a frame holder for holding the fluid containment material to the fluid impermeable/package material.
Figure 18B:
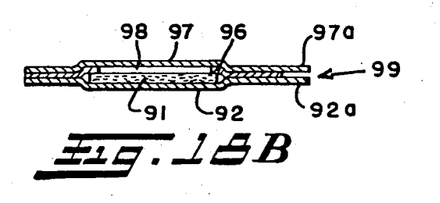
Figure 19:
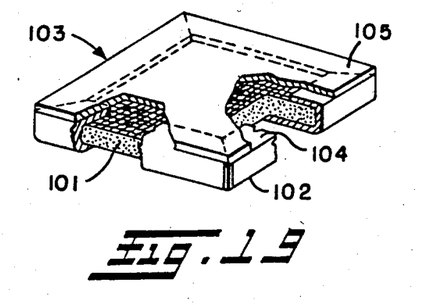
FIG. 19 is an isometric view, partly broken away in section, of a folded over frame/sandwich construction of integral fluid applying device.

Briefly referring to devices 90, 100 in FIGS. 18A, 18B and 19, respective sandwich type fastening techniques for securing respective pads 91, 101 to package material sheets 92, 102 are illustrated. In the integral fluid applying device 93 of FIGS. 18A and 18B, a picture frame type of sheet 94 of rectangular angular configuration having a central opening 95 is secured to the sheet 92, which may be of foil having a plastic liner, such that perimeter edges of the annulus adjacent the opening 95, for example as is shown at 96, overlap a portion of the pad 91 to hold the same in engagement with the package material sheet 92. A cover sheet 97, also, for example, of foil with an inner plastic liner is attached to the sheet 94 to close an internal chamber 98. Various seal techniques may be used for the device 93 to maintain the fluid tight integrity of the chamber 98. For example, the several sheets 92, 94 and 97 may be sealed about the perimeter 99 using thermal sealing techniques, pressure sealing techniques, or the like. Also, if desired, flanges 92a, 97a or other means to facilitate removal of the sheet 97 from the combination of pad 91, sheet 92 and frame 94 may be provided either to permit full removal of the sheet 97 or, alternatively, partial removal thereof while still remaining attached to the remainder of the device 93 as the pad 91 still is exposed for use.

In the integral fluid applying device 103 of FIG. 19 the edges 104 of the sheet 102 are folded up and over the pad 101 to retain the same within a frame-like holder formed by the package material 102, which may be foil lined with a plastic liner, as was described above. A cover sheet 105 may be sealed in position shown in FIG. 19 using the various seal techniques described above. Also, the cover sheet 105 may be removed from the sheet 102 by using a flange (not shown) that may facilitate grasping of the sheet 105 to peel the same partly or wholly off the sheet 102.

The fastening, enclosing and sealing techniques disclosed in FIGS. 18A, 18B and 19 also may be utilized in the various other embodiments of the invention, as may be desired.

Referring back to FIGS. 6A and 6B, a triangle/diamond shape integral fluid applying device 200 is illustrated. Such device includes a diamond shape pad 201 and a diamond shape package material 202, for example of the type described above with reference to the pad and package material 11, 12. The seal zone 203 also is illustrated, and when the device 200 is in closed condition the fluid-tight chamber 204 is provided by the seal 203 and fold 205. In the closed condition of the device 200 pointed tabs 206 are conveniently available for separation and grasping by a user to facilitate opening the device to use the same in the manner described above.

A circular/semi-circular integral fluid applying device 210 is illustrated in FIGS. 7A and 7B in which the pad 211 and package material 212, for example of the type described above with reference to FIGS. 2A-2D are of generally circular shape and fold along the fold line 213 to semi-circular shape. The seal zone 214 also is of annular circular or semi-circular shape, as is illustrated. Moreover, tabs 215 in the package material 212 may be grasped manually by a user to facilitate opening the device from the closed condition shown in FIG. 7A to the open condition of FIG. 7B for use.

A rectangular integral fluid applying device 220 in FIGS. 8A, 8B and 8C includes a rectangular pad 221 of the same shape as the package material 222 of the type described above, for example with reference to FIGS. 2A-2D. The seal zone 223 for the device 220 extends in generally rectangular angular manner from the area 224 which ordinarily would be the fold line, for example at 14 in FIG. 2D, leaving available unsealed flanges 225 which may be grasped to open the device 220. Importantly, the device 220 includes a user grasp tab or handle portion 226. Such handle portion 226 is formed by folding or crimping the package material 222 in the manner shown in FIG. 2B prior to attaching the pad 221 to the surface 227. The two sides 226A, 226B of the package material which form the handle 226 may be heat sealed together so that the junction 228 is in effect one side of the seal zone 223. Alternatively, the seal zone 223 may extend in the manner shown in FIG. 8C into the handle 226 so that the boundary 229 of the handle at which there is a clear gold, analogous to the fold 14 of the device 10, provides a closing side or leg of the seal for the internal chamber of the device 220.

In using the device 220 a user may grasp the flanges 225 and may apply a force to open the seal 223 exposing the pad 221 without actually touching the same or any fluid contained therein. With the device 220 open to the condition shown in FIGS. 8A and 8B, then, the user may grasp the handle 226 and use the latter to rub the device 220 and particularly the pad 221 against a surface to which fluid is to be applied, for example, the skin of a patient. After such use, the device 220 may be discarded. The handle 226 may be employed as part of the several integral fluid applying devices disclosed herein especially to facilitate use without the user having to touch the fluid contained in the pad.

The several embodiments of the invention disclosed herein may be modified to include such a handle 226. Moreover, if desired, the portions of the material 227 respectively above and below the handle and also forming respective parts of the handle 226 may be separate pieces of material and may be securely joined or bonded at the handle area to form the handle during manufacturing of the device 220 or modified devices as mentioned above.

In FIG. 9 an integral fluid applying device 230 is substantially identical to the device 220 except that the pad 231 extends only on one-half portion of the package material 232, particularly that portion identified as 232a. The portion 232b of the package material is used primarily for a cover. The seal zone in the device 230 is not shown, but it would be, for example, of the type shown in FIG. 8C. Moreover, the dashed lines approximately across the middle of the device 230 represent a handle 233 for the device 230 of the type shown at 226 in FIG. 8B.

An integral fluid applying device 240 illustrated in FIG. 10 also includes a pad 241 attached only on one-half portion 242a of the package material 242. The other half 242b of the package material may provide simply a cover for the pad and, if desired, may be removed by tearing the same along the tear line 243. Alternatively, the portion 242b may be folded back or reverse folded to remove any non-sterile surface from exposure to the pad 241 in the manner shown in FIG. 15. When so folded back in the manner shown in FIG. 15, the portions 242a, 242b are positioned back to back or foil to foil and the flanges 244 are positioned as shown in such figure. The device may be grasped by a user, then, and used to apply fluid to a surface.

In addition to the reverse folded form for use of the device 240 in the manner shown in FIG. 15, various other devices, such as devices 10, 30, 40, 200, 210, and the like, may be used in the reverse folded form of FIG. 14. Thus, for example, the device 10 used in the reverse folded form of FIG. 14 would have the flanges 17 near the top, the package material portions 12a, 12b back to back, and the pad 11 fully exposed for wiping against a surface. The user, such as a technician, need not touch the pad portion which is intended to be placed in engagement with the skin of a patient, for example, in either usage technique of FIGS. 14 or 15.

An integral fluid applying device 250 in FIG. 16 includes a towelette 251 attached to package material 252. The package material 252 may be of the type described above. The towelette 251 is formed of absorbent material, such as that disclosed in the '467 patent. The towelette 251 may be folded to a relatively small size to fit within a chamber formed by a sealed package 252. The towelette 251 contains, for example, a cleaning and refreshing fluid, such as that disclosed in the '467 patent, or other fluid material, as may be desired. When the seal on the device 250 is broken and the device is opened, the towelette 251 may be unfolded in the manner shown in FIG. 16 for use to wipe a surface, such as the skin of a person.

It is noted here that although the towelette 251 and the other absorbent materials disclosed herein are most preferably intended ordinarily to contain a fluid to be applied to another surface, for example, when the device is opened, equivalently such absorbent materials may be employed for the purpose of wiping or absorbing materials from an external surface. In such case, the package, such as the package 252 of the device 250, or any of the other packages disclosed herein, may be used for the purpose of maintaining the absorbent material clean or sterile.

Choice of the preferred plastic lined foil material, such as that described above as material 12 in the preferred embodiment of FIGS. 2A-2D, currently is founded on the fact that such material ordinarily is used in conventional alcohol preparation devices, such as the Webcol device mentioned above, is available commercially, and is known to be satisfactory for conventional alcohol preparation and towelette devices. However, the package material may be of other types, as also was mentioned above. An example of another type of package material may be simply a plastic or plastic type of material to which the absorbent material may be directly, e.g. as was described above with reference to FIG. 11, or indirectly, e.g. as was described in connection with FIGS. 2A-2D, connected; a foil; cellulosic materials; and/or various combinations thereof.

Another form of package material may be a wax or paraffin type of material, and this case is illustrated in the device 260 of FIGS. 17A and 17B. In the device 260 the pad 261 is formed of absorbent material of the type described above, such as with respect to the pad 11 of FIGS. 2A-2D, but the package material 262 is the above mentioned wax, paraffin or like material, and most preferably the aforementioned PARAFILM. Such PARAFILM is adequately flexible so that it can be folded at 263 to form a chamber 264 that is sealed about the remaining perimeter of the folded device 260 of FIG. 17B at the seal 265. Flanges 266 are available to be held by a user for applying pressure to breach the seal integrity opening the device 260 to the form illustrated in FIG. 17A for use in the various manners described above.

Figure 20:
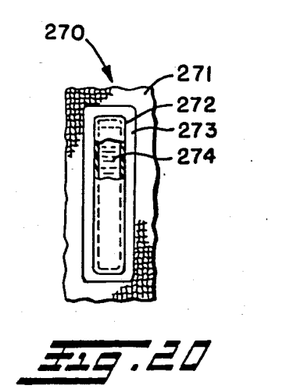
FIG. 20 is a fragmentary plan view, partly broken away in section, of an alternate type of integral fluid applying device having a breakable vessicle within fluid permeable material.
Figure 21:
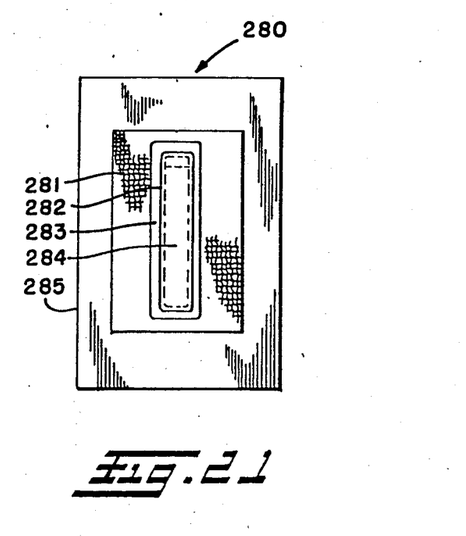
FIG. 21 is a plan view of an integral fluid applying device of the type shown in FIG. 20 contained within a protective package.

Alternate forms of the invention are shown in FIGS. 20 and 21. In those embodiments there are devices 270, 280 which are comprised of fluid absorbent or permeable material 271, 281, respectively, and a breakable vessicle 272, 282 contained within respective chambers 273, 283 formed by the absorbent material. The vessicles 272, 282 contain liquid 274, 284 and ordinarily prevent loss, e.g. by leakage or evaporation, or contamination of such liquid during storage. A user may apply pressure to the respective devices 270, 280 in a manner such that the pressure is transferred to the respective vessicles 272, 282 to break the same allowing the liquid 274, 284 to permeate the material 271, 281 while the material itself confines or restricts the vessicle and any pieces thereof to the chamber 273, 283. The liquid in the material 271, 281, then, may be applied in a manner similar to that described above, for example by wiping the device 270, 280 on the skin of a patient, or the like. An example of a satisfactory vessicle 272, 282 may be a gelatin capsule type of structure that may crack upon application of pressure thereto but which will not produce multiple pieces upon cracking.

The device 270 may be contained in a box, dispenser, or other structure that will maintain the device 270 satisfactorily clean or sterile, as may be desired, prior to use thereof. On the other hand, the device 280 preferably is contained within an impermeable package 285. Such package 285 may be formed of metal foil, plastic lined metal foil, wax, paraffin, or the various other materials described above for use as package materials. The package material 285 may be opened in the manner disclosed in FIG. 1B, i.e. according to the prior art technique, or the package material 285 may be, and most preferably is, attached to the absorbent material 281 to form an integral device therewith and may be capable of opening in one of the manners described above that does not destroy the integrity of the connection between the absorbent material 281 and package material 285.

Figure 22:
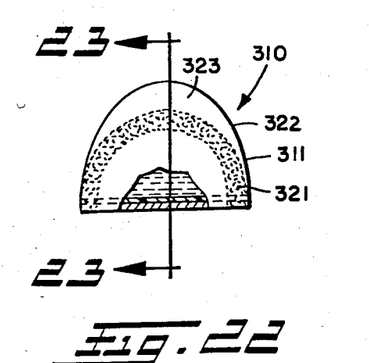
FIG. 22 is a plan view, partly broken away in section, of a one piece fluid applying device in accordance with the present invention.
Figure 23:
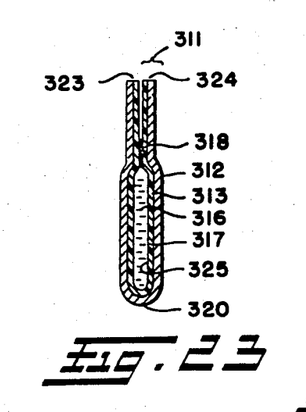
FIG. 23 is a section view of the device of FIG. 22 looking generally in the direction of the arrows 23—23.
Figure 24:
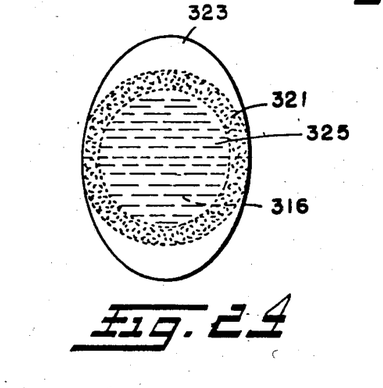
FIG. 24 is a plan view of the device of FIG. 22 with the flexible material thereof being fully open to expose the liquid coating the same for application to an external surface.

As distinguished from the intentionally separable parts of the prior art device 1, the fluid applying device 310 in accordance with the present invention shown in FIGS. 22, 23 and 24 is formed by a single sheet of material for containing liquid in isolation in a chamber and for applying that liquid upon opening the device to use a surface of the sheet to apply the liquid. The device does not have intentionally separable parts and can in fact be stored and used without destroying the attached or structural integrity thereof. The principal difference between the device 310 and the earlier described device 10, for example, is that the device 310 does not require a separate fibrous or other material absorbent pad 11, for example.

Referring now to FIGS. 22-24, the one piece fluid applying device 310 in accordance with the present invention is formed of a single piece of flexible material 311. The material 311 may be of the types disclosed in the '467 patent or of the type used in the Webcol device; an example of such material includes a metal foil 312 having an inner thermoplastic liner 313. However, in the preferred embodiment and best mode of the present invention, the material 311 is formed of a plastic, paraffin or wax material, such as that sold under the trademark PARAFILM by the American Can. Company. Such PARAFILM material is illustrated at 315 in FIG. 25.

Figure 25:
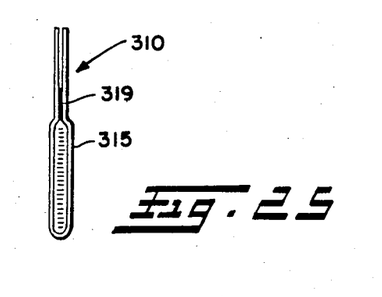
FIG. 25 is a section view of a modified one piece fluid applying device in which the flexible material is comprised of a paraffin or wax material.

The material 311, 315 or any other material of which a one piece fluid applying device in accordance with the invention is formed should be relatively flexible, should be unaffected by the liquid, or other fluid, 316 contained in the chamber 317 formed by the material, and should be capable of being sealed, for example, by the seal represented at 318 in FIG. 23 and 319 in FIG. 25. The flexible material should be adequately strong to resist undesired penetration. The seal should have suitable longevity to avoid leakage or evaporation of liquid therefrom. The liquid 316 may be of the type that cleanses, sterilizes, refreshes, or the like.

The material 311 provides a plurality of functions. Such material has a fold 320 that provides part of the sealing function for the chamber 317 along a continuous linear edge thereof. The seal 318, on the other hand, provides a fluid tight seal for the chamber 317 in the seal zone 321 that extends approximately along or nearly parallel to a perimeter of the device 310 at or near the edge 322 thereof. Most preferably the shape of the material 311 is oval when open, as is seen in FIG. 24, and is of semi-oval configuration when folded in the manner illustrated in FIGS. 22 and 23. On the other hand, preferably the seal zone 321 is approximately a semi-circular annulus when the device is folded and would appear generally circular when the device 310 is open in the manner shown in FIG. 24. As a result of such oval/circular or semi-oval/semi-circular relationships, portions, tabs, or extensions 323, 324 of the flexible material 311 are relatively accessible and are unsealed so that they may be grasped manually by a user. Such a user may apply force to such portions 323, 324 tending to separate them in order to breach the integrity of the seal 318 opening the folded device to its open form shown in FIG. 24. Upon such opening the liquid 316 becomes accessible.

Accordingly, further functions of the material 311 are to provide the tab portions 323, 324 to facilitate opening of the device 310 and, very importantly, to provide the wall surface area 325 (FIG. 24), which previously provided the boundary walls for the chamber 317, for applying the liquid 316 to another surface, object or the like.

A user may use the device 310 after separating the tab portions 323, 324 to open the device in the manner shown in FIG. 24, by grasping one of the tab areas 323, for example, between the thumb and a finger; and using other fingers of the same hand behind the surface 325 to provide support thereby, may wipe the surface area 325 against an external surface or device intended to have the liquid 16 applied thereto.

An advantage of using the thermoplastic lined material 311 is that the seal 318 may be formed by appying heat to the seal zone 21, whereupon the plastic material of opposed material portions when the device is folded will heat seal to each other. Alternatively and/or additionally mechanical pressure may be applied to the seal zone 321 to form the seal 318. As a further alternative, fluid, semi-solid or solid means may be applied at the seal zone 321 to form or to help form the seal 318. An advantage of using the fold 320 as part of the seal for the chamber 317 is that such fold area will provide a rather strong seal integrity thereat, thus reducing portions of any seal that ordinarily might encounter a flaw.

It is desirable that the surface area 325 have a relatively high surface energy so that the liquid 316 will substantially uniformaly coat the surface. Accordingly, the liquid should have a satisfactorily low surface tension in order to maintain such coating uniformity or, at the least, complete coating of the surface 325. On the other hand, the liquid should have an adequately high surface tension to facilitate containment thereof in the chamber 317 and sealing of such chamber. Examples of such liquid may be an alcohol or alcohol-containing solution, such as a 70% isopropyl alcohol in solution with water. The alcohol also may be a methyl alcohol or an ethyl alcohol. Examples of alcohol that may be used are as follows: polyoxyethylene sorbitan monolaurate, polyoxyethylene sorbitan monopalmitate, polyoxyethylene sorbitan monostearate, and polyoxyethylene sorbitan monooleate. Another example is a material sold under the name Nonidet P-40, which is an octyl phenol ethylene oxide condensate containing an average of 9 moles ethylene oxide per molecule. Moreover, if desired, to assure good coating of the liquid over the surface 325, a wetting agent may be used in solution with the liquid 316. An example of such a wetting agent is sold as Wetting Agent H by J. T. Baker Diagnostics Chemical Co., Bethlehem, Pa.

Briefly referring to FIG. 25, the preferred embodiment and best mode of the present invention is embodied in the device 10a. Such device is substantially the same as that described above with reference to FIGS. 22-24, but as was mentioned earlier, the material 315 of which the device is formed is comprised of a plastic, paraffin or wax material. Such material 315 has a good flexibility characteristic and a good integrity characteristic. Moreover, such material is relatively light weight and inexpensive. Additionally, such material 315 is directly responsive to application of heat to form the seal 319. The shape of the device 10a would be preferably the same as the shape illustrated in FIGS. 22-24, namely, an oval shape having a circular seal zone when the device is open; and a semi-oval shape with a semi-circular seal zone when the device is folded in the manner illustrated in FIG. 25.

Figure 26:
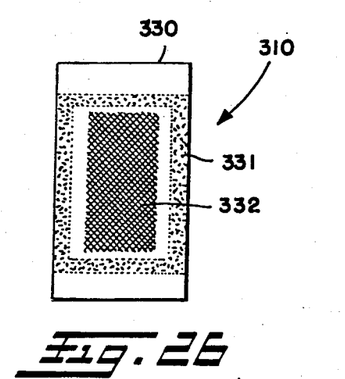
FIG. 26 is a further modified device in which a surface of the flexible material that forms boundary walls for the fluid chamber is roughened to facilitate holding fluid material thereon.

Either of the devices 310, 310a also may be formed in shapes other than oval ones. For example, as is shown in FIG. 26, such devices may be rectangular, or they may be diamond shape when open or any other shape, as may be desired. An advantage to a diamond shape configuration, which is not shown herein, is the availability of the free apexes, i.e., those that do not join a fold, of the triangles that are formed when the device is folded to form a chamber, such as the chamber 317, for use to facilitate manual grasping of the device to open the same, etc., as was described above.

As is seen in FIG. 26, a one piece fluid applying device 310b in accordance with the invention is formed of a rectangular flexible material 330 having a rectangular seal zone 331. The device 310b is illustrated in open position ready for use to apply fluid contained in the area 332 to an external surface. The surface 332, moreover, has been roughened or knurled or otherwise pretreated or prepared so as to increase the quantity of liquid that can be contained by or adhered to the surface. Roughening of the surface 332 not only will increase the quantity of fluid that can be adhered thereto but also may be used to effect some abrasion of a surface to which the liquid is to be applied thereby to assist in effective application of the liquid to such external surface.

Further to assure the effective coating of the external surface with such liquid, it is important that the liquid contained by the surface 325 or 332 of the present invention not undergo covalent bonding with the liquid.

Figure 27:
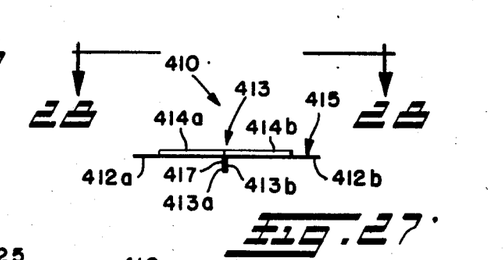
FIGS. 27 and 28 are end elevation and top views of a modified device according to the invention.
Figure 28:
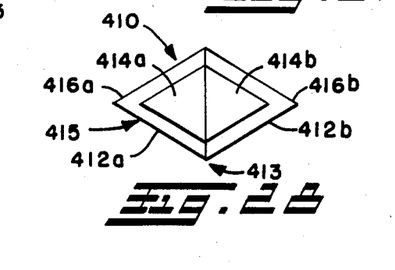

Briefly referring to FIGS. 27 and 28, a triangular (when folded) or diamond shape (when unfolded) device 410 according to the invention is shown. The device 410 is comprised of two separate sheets of fluid impermeable material 412a, 412b, and these are securely joined or bonded at a junction 413 of two downwardly turned tabs 413a, 413b (downwardly means out of the major planar extent of the material 412a, 412b but need not actually be facing down). Such junction 413 may be formed by heat sealing, crimping, force application, adhesive or other material, etc., in order to secure effectively as an integral or single piece the two pieces 412a, 412b. A pad 414a, 414b is adhered on each piece of material 412a, 412b (or if desired only on one piece, or the pads may be replaced by a single pad adhered to one or to both of the pieces 412a, 412b), and fluid is contained or is placed for containment in the pad. The pieces 412a, 412b may be folded over into overlying relation and the seal area 415 may be sealed, as above, to close the internal chamber of the device 410.

To use the device 410 a user would apply force to the apex of the triangular folded and sealed device at the opening points 416a, 416b, whereupon the shape of the device 410 helps balance application of the force along both seal lines from the points 416a, 416b to the secure junction 413 and handle 417 formed thereat by the tabs 413a, 413b. With the pad(s) thus exposed, the device 410 may be used to wipe fluid in the pad onto a surface.

STATEMENT OF INDUSTRIAL APPLICATION

With the foregoing in mind, it will be appreciated that the fluid applying devices in accordance with the present invention may be used to maintain relatively clean or sterile conditions of a fluid applying device and to keep the fluid ready for use, e.g. preventing evaporation or leakage thereof. The fluid may be a cleansing, refreshing, sterilizing, or like fluid. The invention also relates to methods of making the integral fluid applying devices and of using the same for cleaning, refreshing, sterilizing or like fluid applying purposes.

I claim:

1. A combined fluid storage container and applicator device for relatively inviscid fluids, said device comprising a sheet-like fluid impermeable material having generally symmetrical halves positioned in generally flat parallel overlying relation to each other, a pair of respective edges of said material halves being securely joined along an effective fold line as an effectively single integral sheet of said material halves, temporary seal means sealing said halves to each other along a temporary seal line beginning and ending at said fold line forming a cavity and enclosing fluid between said halves and within said temporary seal line and said fold line, a fluid in said cavity, and separation means for simultaneously applying separating force substantially symmetrically to both said halves of said sheet and to said temporary seal means without tearing said sheet, said separation means including means for applying simultaneously in at least two opposing directions continuous separating force out of the plane and at an angle that is no greater than about a perpendicular to the generally planar extent of the device to open said temporary seal means along at least a portion of the length of said seal line to form a flat surface covered with the fluid while the integrity of said sheet is maintained.

2. The device of claim 1, wherein said material halves are originally separate pieces of sheet material, and said secure joining thereof at said fold line comprises a secure fastened junction of said pieces.

3. The device of claim 1, further comprising a fluid retaining pad disposed in said cavity and adhered to said material.

4. A device of claim 3, wherein the peripheral border of said pad are spaced inwardly of said temporary seal line.

5. The device of claim 3, said fluid retaining pad covers approximately one-half the surface of said material enclosed by said temporary seal line when said material is unfolded whereby the other half of said material enclosed by said temporary seal line comprises a cover for said cavity.

6. A device of claim 1, wherein said temporary seal line comprises the inner border of a temporary seal zone and is spaced inward from the periphery of said sheet of metal.

7. The device of claim 1, wherein said separation means includes means for facilitating applying force to said temporary seal means to breach the same and to open said chamber for access to the fluid therein, said means for facilitating comprising protruding opposite unsealed portions of said halves of said sheet of impermeable material.

8. A device of claim 1, wherein said temporary seal line is spaced inward from the periphery of said sheet of material to define between said periphery and said temporary seal line a seal zone as a manually graspable perimeter portion of the device outside said temporary seal line.

9. The device of claim 1, said fold line comprising a peripheral seal line at the borders of two equally flat halves of said material and along which a continuation of simultaneous separating forces separates such two halves of said material.

10. The device of claim 1, further comprising handle means for facilitating manual grasping of the device for use, said handle means comprising a crimp in said impermeable material.

11. The device of claim 10, said handle means comprising approximately a 90° reverse fold in said sheet of impermeable material out of the major plane of said sheet material.

12. The device of claim 1, wherein the fluid is sterile and comprises at least one of alcohol and iodine.

13. The device of claim 1, said material comprising foil having an inner plastic liner.

14. The device of claim 1, wherein said sheet-like fluid impermeable material comprises at least paper-like material lined by and structurally supporting a thin metallic material layer.

15. The device of claim 3, wherein said adherence is produced by a relatively inviscid fluid-like material.

* * * * *